(12) United States Patent
Kim et al.

(10) Patent No.: US 8,803,968 B2
(45) Date of Patent: Aug. 12, 2014

(54) APPARATUS FOR DETECTING PARTICLES IN FLAT GLASS AND DETECTING METHOD USING SAME

(75) Inventors: Hyun-woo Kim, Asan-si (KR); Misun Kim, Asan-si (KR); So-ra Yu, Asan-si (KR); Gahyun Kim, Asan-si (KR); Taeho Keem, Asan-si (KR); Changha Lee, Asan-si (KR)

(73) Assignee: Samsung Corning Precision Material Co., Ltd. (KR)

( * ) Notice: Subject to any disclaimer, the term of this patent is extended or adjusted under 35 U.S.C. 154(b) by 178 days.

(21) Appl. No.: 13/049,425

(22) Filed: Mar. 16, 2011

(65) Prior Publication Data
US 2012/0194668 A1  Aug. 2, 2012

(30) Foreign Application Priority Data
Jan. 31, 2011 (KR) .................. 10-2011-0009258

(51) Int. Cl.
*H04N 7/18* (2006.01)

(52) U.S. Cl.
USPC .................................. 348/135; 348/E07.085

(58) Field of Classification Search
USPC ............................................ 348/135, E7.085
See application file for complete search history.

(56) References Cited

U.S. PATENT DOCUMENTS

| | | | |
|---|---|---|---|
| 3,652,863 A * | 3/1972 | Gaskell et al. ............. | 250/559.18 |
| 7,369,240 B1 * | 5/2008 | Abbott et al. .................. | 356/429 |
| 2005/0018199 A1 | 1/2005 | LeBlanc | |
| 2005/0122508 A1 * | 6/2005 | Uto et al. .................... | 356/237.2 |

(Continued)

FOREIGN PATENT DOCUMENTS

| | | |
|---|---|---|
| CN | 101226158 | 7/2008 |
| CN | 101819165 | 8/2013 |

(Continued)

OTHER PUBLICATIONS

Machine Translation of Japanese Patent application: JP 2010230368 A.*

(Continued)

*Primary Examiner* — Christopher S Kelley
*Assistant Examiner* — Ana Picon-Feliciano
(74) *Attorney, Agent, or Firm* — Cantor Colburn LLP

(57) ABSTRACT

The present invention relates to an apparatus for detecting particles in flat glass and a detecting method using the same. The present invention provides an apparatus for detecting particles in flat glass, comprising: an illumination unit which is installed in one region selected from upper and lower regions on the basis of flat glass; a first polarizer which is installed between the illumination unit and the flat glass, and has a first polarization direction; a first camera and a second camera which are installed in the opposite direction where the illumination unit is installed on the basis of the flat glass; a second polarizer which is equipped in a space between the first camera and the flat glass, and has a polarization direction in the range of 0° to 20° that is different from the polarization direction of the first polarizer; a fourth polarizer which is equipped in a space between the second camera and the flat glass, and has a polarization direction in the range of 70° to 90° that is different from the polarization direction of the first polarizer; and a processor which receives images obtained from the first camera and the second camera, and decides whether defects are benign particles or malignant particles.

11 Claims, 6 Drawing Sheets

(56) References Cited

U.S. PATENT DOCUMENTS

| | | | |
|---|---|---|---|
| 2009/0141264 A1* | 6/2009 | Shibata et al. | 356/51 |
| 2009/0324056 A1* | 12/2009 | Sun | 382/145 |
| 2010/0271473 A1* | 10/2010 | Aiko et al. | 348/92 |
| 2010/0309307 A1* | 12/2010 | Jin | 348/86 |

FOREIGN PATENT DOCUMENTS

| | | | |
|---|---|---|---|
| JP | 63-163152 A | | 7/1988 |
| JP | 07-270325 A | | 10/1995 |
| JP | 2000028546 A | | 1/2000 |
| JP | 2001-108626 | | 4/2001 |
| JP | 2009-271497 A | | 11/2009 |
| JP | 2010230368 | | 10/2010 |
| JP | 2010230368 A | * | 10/2010 |
| KR | 1020080067573 A | | 7/2008 |
| WO | 2010/097055 A1 | | 9/2010 |
| WO | WO 2010097055 A1 | * | 9/2010 |

OTHER PUBLICATIONS

Extended European Search Report for Application No. 11163157.8-1524 dated Sep. 1, 2011.

* cited by examiner

Fig. 6
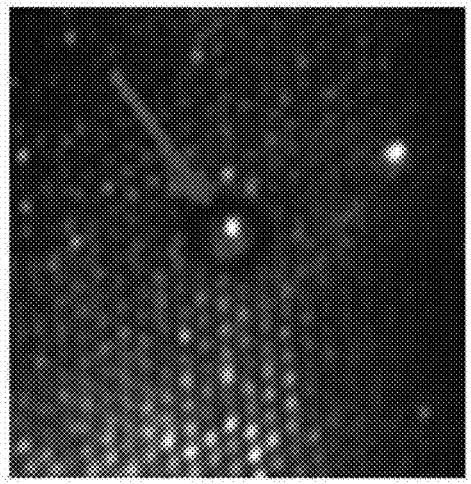
(a)
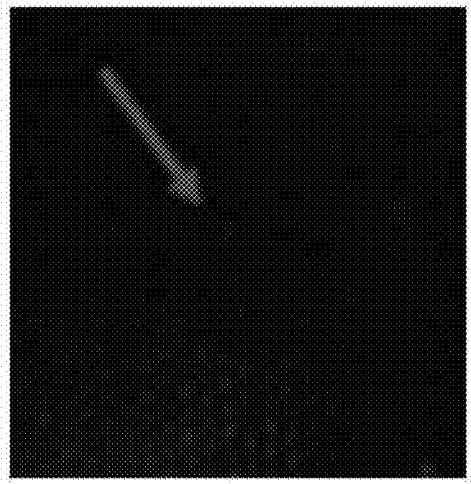
(b)
Fig. 7
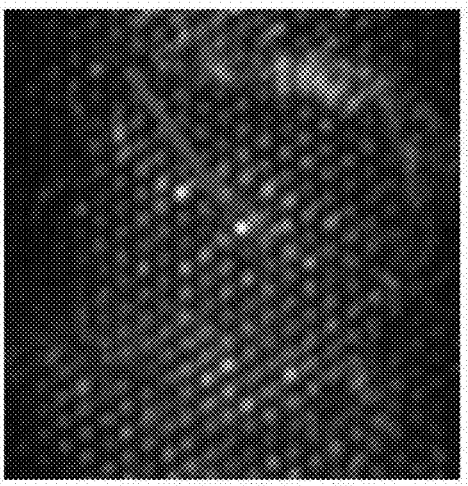
(a)
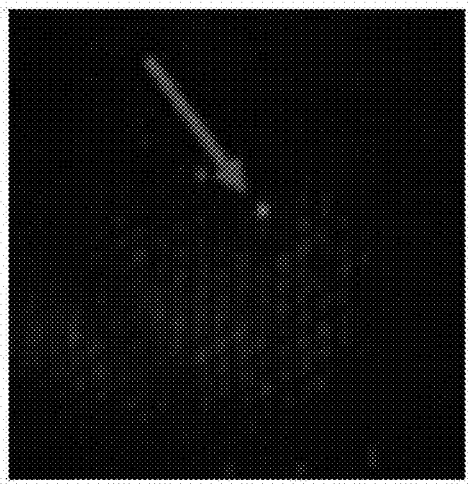
(b)

APPARATUS FOR DETECTING PARTICLES IN FLAT GLASS AND DETECTING METHOD USING SAME

BACKGROUND OF THE INVENTION

1. Field of the Invention

The present invention relates to an apparatus for detecting particles in flat glass and a detecting method using the same, and more specifically, to an apparatus for detecting particles in flat glass and a detecting method using the same for exactly inspecting particles such as metal and ceramic components that largely influence the inside quality of flat glass.

2. Description of the Related Art

During a flat glass fabrication process, inside particles which are generated when a glass material is melted and made into a flat plate include bubbles, metal, ceramic components and others. Since these inside particles have a large impact on the quality of flat glass, an exact inspection technology is essential. In addition, according to the components of the inside particles, degrees of the quality of flat glass being affected are different. Therefore, it is necessary to distinguish and inspect the components of the inside particles. Particularly, among these inside particles, bubble components do not have a large effect, whereas metal or ceramic components do. Accordingly, even though certain glass contains these bubble components, it is known that the glass can be used as solar cell protecting glass.

As for an inspection device for detecting defects among a transparent plate-shaped body, BF (Bright Field) optical systems and DF (Dark Field) optical systems are widely employed.

A bright field optical system will be described briefly as follows. FIG. 1 shows a bright field optical system for detecting defects which exist among a transparent plate-shaped body. Referring to FIG. 1, a bright field optical system includes a sensor camera 3 which is positioned in the regular reflection direction of a light source 2 with respect to a transparent plate-shaped body 1. Therefore, a light beam radiated from the light source 2 mostly reaches at the sensor camera 3 via two ray paths 2a and 2b, wherein one ray path 2a of the ray paths 2a and 2b corresponds to a light beam reflected against a top surface of the plate-shaped body 1 and the other ray path 2b corresponds to a light beam reflected against a bottom surface of the transparent plate-shaped body. The sensor camera 3 becomes a bright field onto which an image reflected by the ray paths 2a and 2b as above.

In such a bright field optical system, inspections are carried out by photographing reflected images for a transferred transparent plate-shaped body. In the photographing process, the bright field optical system obtains a real image and a virtual image (a shadow) by a reflection light source and it is possible to detect whether the flat glass has a defects or not.

Next, a dark field optical system will be described briefly as follows. FIG. 2 shows a dark field optical system for detecting defects which exist among a transparent plate-shaped body. Referring to FIG. 1, in a dark field optical system, a sensor camera 5 is disposed on a top surface of a transparent plate-shaped body 1, and a light source 6 is disposed on a bottom surface of the transparent plate-shaped body 1, thereby photographing images by using transmitted light instead of reflected light. In other words, the dark field optical system detects defects 4 such as impurities which are existing among the transparent plate-shaped body 1 by collecting dark field components in transmitted light beams 7.

However, when the inspections are carried out by the prior bright field optical systems or the dark field optical systems, although it is easy to perceive the exact position of the defects, it is hard to decide whether the discovered defects largely affect the quality of glass that contains metal and ceramic components, or the defects does not give much effect on the quality of glass that contains bubble components.

SUMMARY OF THE INVENTION

It is therefore an object of the present invention to provide an apparatus for detecting particles in flat glass and a detecting method using the same for exactly distinguishing particles contained in the inside of flat glass into defects that influence the glass quality and defects that do not affect the glass quality.

To achieve the above object, the present invention provides an apparatus for detecting particles in flat glass, the apparatus comprises: an illumination unit which is installed in one region selected from upper and lower regions on the basis of flat glass; a first polarizer which is installed between the illumination unit and the flat glass, and has a first polarization direction; a first camera and a second camera which are installed in the opposite direction where the illumination unit is installed on the basis of the flat glass; a second polarizer which is equipped in a space between the first camera and the flat glass, and has a polarization direction in the range of 0° to 20° that is different from the polarization direction of the first polarizer; a fourth polarizer which is equipped in a space between the second camera and the flat glass, and has a polarization direction in the range of 70° to 90° that is different from the polarization direction of the first polarizer; and a processor which receives images obtained from the first camera and the second camera, and decides whether defects are benign particles or malignant particles.

Further, to achieve the above object, the present invention provides a flat glass particle detecting method for distinguishing whether defects contained in flat glass are benign particles or malignant particles, the method comprises the steps of: a first step of obtaining an image by irradiating polarized light on the flat glass, and by photographing light transmitted through a polarizer which has a polarization direction in the range of 0° to 20° that is different from a polarization direction of the polarized light; a second step of obtaining an image by irradiating polarized light on the flat glass, and by photographing light transmitted through a polarizer which has a polarization direction in the range of 70° to 90° that is different from the polarization direction of the polarized light; and a third step of distinguishing whether defects contained in the flat glass are malignant particles that affect the glass quality or benign particles that do not affect the glass quality, by comparing the image obtained from the first step with the image obtained from the second step, wherein the first step and the second step are carried out at the same time or performed regardless of order.

According to the apparatus for detecting particles in flat glass and the detecting method using the same of the present invention, it is possible to decide whether defects contained in the flat glass are benign particles such as bubble components or malignant particles such as metal or ceramic components. Therefore, with the use of polarizers, it is also possible to clearly distinguish a case where particles such as bubble components are contained in flat glass from a case where particles such as metal or ceramic components are contained in the flat glass.

BRIEF DESCRIPTION OF THE DRAWINGS

FIG. 6 shows photos for photographing flat glass that contains defects with bubble components of 200 um size by using the photographing device configurations suggested in FIG. 4.

FIG. 7 shows photos for photographing flat glass that contains defects with metal components of 200 um size by using the photographing device configurations suggested in FIG. 4.

BRIEF EXPLANATION OF REFERENCE SYMBOLS

Figure 1:
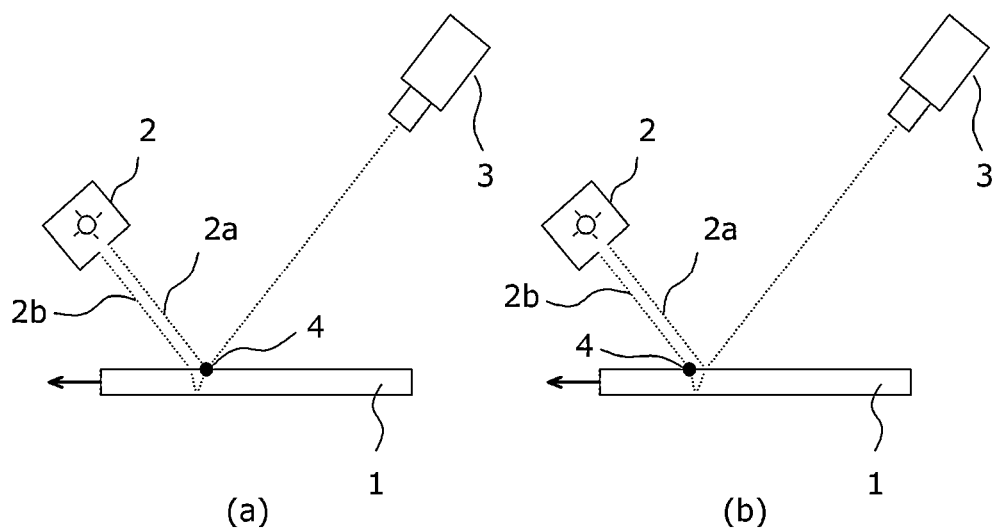
FIG. 1 is a view showing a bright field optical system for detecting defects existing on a transparent plate-shape body.
Figure 2:
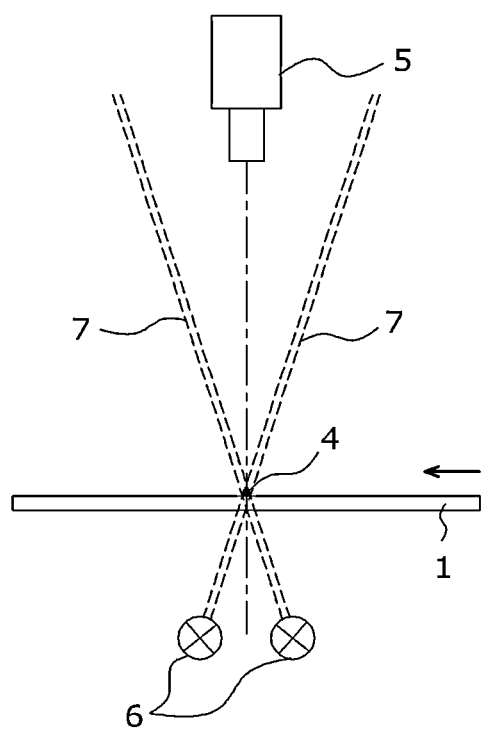
FIG. 2 is a format diagram illustrating a dark field optical system for detecting defects existing on a transparent plate-shaped body.

| | |
|---|---|
| 1: transparent plate-shaped body | 4: particles |
| 10: first camera | 11: first polarizer |
| 13: second polarizer | 15: third polarizer |
| 17: fourth polarizer | 20: second camera |
| 31: first illumination unit | 33: second illumination unit |
| 60: first photographing device | 70: second photographing device |

DETAILED DESCRIPTION OF PREFERRED EMBODIMENTS

Reference will now be made in greater detail to preferred embodiments of an apparatus for detecting surface defects of a glass substrate according to the invention, examples of which are illustrated in the accompanying drawings. Wherever possible, the same reference numerals will be used throughout the drawings and the description to refer to the same or like parts.

Hereinafter, the preferred embodiments, advantages and features of an apparatus for detecting particles in flat glass and a detecting method using the same in accordance with the present invention will be more fully described in reference to the accompanied drawings.

Figure 3:
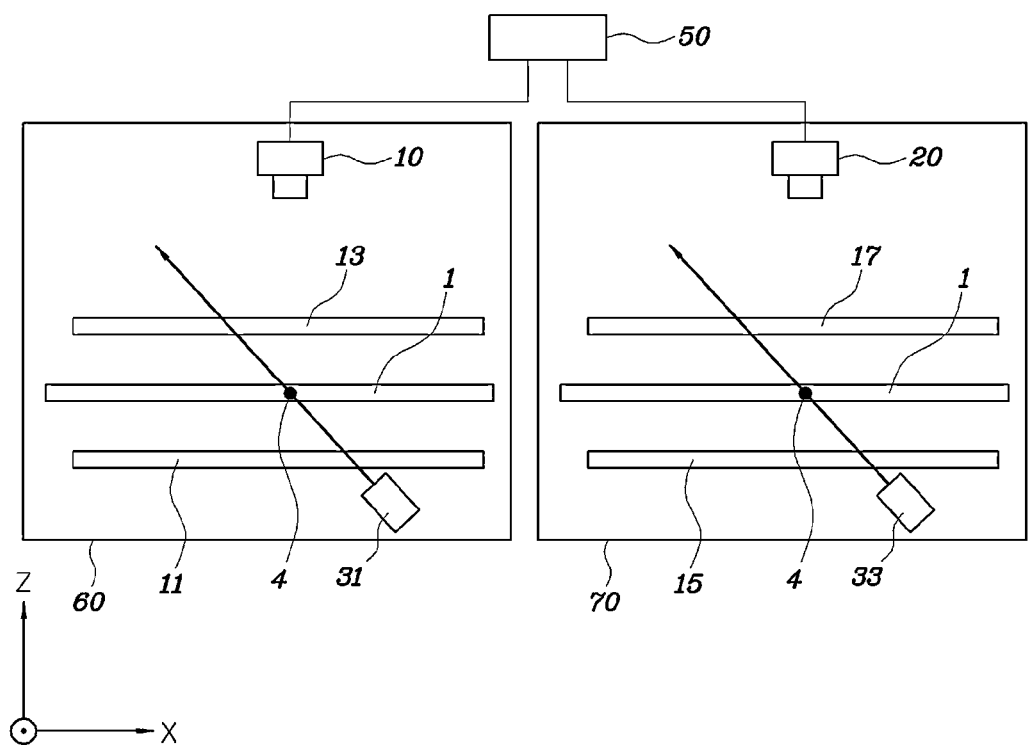
FIG. 3 is a format diagram of an apparatus for detecting particles in flat glass of one embodiment in accordance with the present invention.

FIG. 3 is a format diagram of an apparatus for detecting particles in flat glass of one embodiment in accordance with the present invention. The apparatus for detecting particles on flat glass in accordance with the present invention comprises: a first photographing device 60 and a second photographing device 70 which photograph defects 4 attached or contained in a transparent plate-shaped body 1; and a processor 50 which distinguishes the defects 4 from photographed images.

The first photographing device 60 comprises: a first illumination unit 31 which irradiates light on the transparent plate-shaped body 1 in one direction selected from upper and lower directions of the transparent plate-shaped body 1; a first polarizer 11 and a second polarizer 13 which are respectively installed in the upper and lower parts of the transparent plate-shaped body 1, and have roughly parallel polarization directions; and a first camera 10 which is installed in the opposite direction to the first illumination unit 31 on the basis of the transparent plate-shaped body, and photographs light transmitted through a polarizer which is installed in the opposite direction to the first illumination unit 31 on the basis of the transparent plate-shaped body, among the first polarizer 11 and the second polarizer 13. Here, the meaning of having the roughly parallel polarization directions indicates that the polarization directions of the first polarizer 11 and the second polarizer 13 have a difference in the range of 0° to 20° approximately.

The second photographing device 70 comprises: a second illumination unit 33 which irradiates light on the transparent plate-shaped body 1 in one direction selected from upper and lower directions of the transparent plate-shaped body 1; a third polarizer 15 and a fourth polarizer 17 which are respectively installed in the upper and lower parts of the transparent plate-shaped body 1, and have roughly mutually-vertical polarization directions; and a second camera 20 which is installed in the opposite direction to the second illumination unit 33 on the basis of the transparent plate-shaped body, and photographs light transmitted through a polarizer which is installed in the opposite direction to the second illumination unit 33 on the basis of the transparent plate-shaped body, among the third polarizer 15 and the fourth polarizer 17. Here, the meaning of having the roughly vertical polarization directions indicates that the polarization directions of the third polarizer 15 and the fourth polarizer 17 have a difference in the range of 70° to 90° approximately.

The processor mutually compares defect images taken by the first photographing device 60 with defect images taken by the second photographing device 70 with respect to the same defects 4 which are attached or contained in the transparent plate-shaped body 1, and decides whether the corresponding defects are malignant particles that influence the glass quality or benign particles that do not influence the glass quality, wherein the processor may be realized as a computer or the like including an image processor and an arithmetic operator.

Although particles such as bubble components are contained in the transparent plate-shaped body 1 for protecting a solar cell, the bulk of the incident sunlight is transmitted while the sunlight is partially refracted. Thus, it is not problematic to use the transparent plate-shaped body for protecting the solar cell. So, the defects including the bubble components contained in the transparent plate-shaped body 1 for protecting the solar cell are classified as the benign particles. On the contrary, defects which reflect and/or diffuse the sunlight such as metal or ceramic materials inside the transparent plate-shaped body 1 for protecting the solar cell are problematic because they tend to reflect and/or diffuse the incident sunlight. Accordingly, these defects having the reflecting and/or diffusing properties inside the transparent plate-shaped body 1 for protecting the solar cell are classified as the malignant particles.

From now on, like illustrated in FIG. 3, the first photographing device 60 and the second photographing device 70 will be described in the following structure. The first photographing device 60 comprises: the first polarizer 11 and the second polarizer 13 respectively installed in the lower and upper parts of the transparent plate-shaped body 1; the first illumination unit 31 for irradiating the light in the upper direction ("z" direction) in the lower part of the transparent plate-shaped body 1; and the first camera 10 positioned in the upper part of the transparent plate-shaped body 1. The second photographing device 70 comprises: the third polarizer 15 and the fourth polarizer 17 respectively installed in the lower and upper parts of the transparent plate-shaped body 1; the second illumination unit 33 for irradiating the light in the upper direction ("z" direction) in the lower part of the transparent plate-shaped body 1; and the second camera 20 positioned in the upper part of the transparent plate-shaped body 1. Further, it is given that the first polarizer 11, the second polarizer 13, and the third polarizer 15 have polarization directions for transmitting the light only in the x direction while the fourth polarizer 17 has a polarization direction for transmitting the light only in the y direction.

First, a case where defects including bubble components are contained in the transparent plate-shaped body 1 for protecting the solar cell will be described as follows. As the light emitted from the first illumination unit 31 passes through the first polarizer 11, the light only in the x direction is projected on the transparent plate-shaped body 1. Although the projected light is partially refracted by the defects 4 as passing through the transparent plate-shaped body 1, any diffusion or reflection does not occur whereby the light in the x direction is incident on the second polarizer 13 without a change in an optical axis. Since the second polarizer 13 is designed to have the same optical axis as that of the first polarizer 11, the light incident on the second polarizer 13 is transmitted as it is and reaches the first camera 10. Thus, an image obtained by the first camera 10 as passing through the bubble components contained in the transparent plate-shaped body 1 produces a bright image photo. Meanwhile, as the light emitted from the second illumination unit 33 passes through the third polarizer 15, the light only in the x direction is projected on the transparent plate-shaped body 1. Although the projected light is partially refracted by the defects 4 as passing through the transparent plate-shaped body 1, any diffusion or reflection does not occur whereby the light passing through the transparent plate-shaped body 1 is formed as the x-directional light without a change in an optical axis, and is incident on the fourth polarizer 17. Since the fourth polarizer 17 is designed to have an optical axis vertical to that of the third polarizer 15, the light incident on the fourth polarizer 13 is cut off and cannot reach the second camera 20. Accordingly, an image obtained by the second camera 20 as passing through the bubble components contained in the transparent plate-shaped body 1 produces a dark image photo. That is to say, it would be perceived that when the transparent plate-shaped body 1 containing the defects 4 with the bubble components is photographed, the first photographing device 60 obtains a bright image but the second photographing device obtains a dark image.

Next, a case where defects such as metal or ceramic components are contained in the transparent plate-shaped body 1 for protecting the solar cell will be described as follows. As the light emitted from the first illumination unit 31 passes through the first polarizer 11, the light only in the x direction is projected on the transparent plate-shaped body 1. Since diffusion or reflection occurs by the defects 4 containing the metal or the ceramic components as the projected light passes through the transparent plate-shaped body 1, the x-directional light is incident on the second polarizer 13 after being diffused in various directions. Further, because the second polarizer 13 is designed to have the same optical axis as that of the first polarizer 11, among the lights incident on the second polarizer 13, the lights having the other directions except the x direction are cut off while the light only in the x direction is transmitted and reaches the first camera 10. Thus, an image obtained by the second camera 20 after passing through the transparent plate-shaped body 1 containing the defects with the metal or ceramic components by the second photographing device 70 is relatively bright, compared to an image obtained by the second camera 20 after passing through the transparent plate-shaped body 1 containing the bubble components. In the meantime, as the light emitted from the second illumination unit 33 passes through the third polarizer 15, the light only in the x direction is projected on the transparent plate-shaped body 1. Since diffusion or reflection occurs by the defects 4 containing the metal or the ceramic components as the projected light passes through the transparent plate-shaped body 1, the x-directional light is incident on the fourth polarizer 17 after being diffused in various directions. Further, because the fourth polarizer 17 is designed to have an optical axis vertical to that of the third polarizer 15, among the lights incident on the fourth polarizer 17, the lights having the other directions except the y direction are cut off while the light only in the y direction is transmitted and reaches the second camera 20. Thus, an image obtained by the first camera 10 after passing through the transparent plate-shaped body 1 containing the defects with the metal or ceramic components by the first photographing device 60 is relatively bright, compared to an image obtained by the first camera 10 after passing through the transparent plate-shaped body 1 containing the bubble components. That is to say, compared to a case where the transparent plate-shaped body containing the bubble defects is photographed, it would be perceived that when the transparent plate-shaped body 1 containing the metal or ceramic defects 4 is photographed, the first photographing device 60 obtains a relatively dark image while the second photographing device 70 obtains a relatively bright image.

Hereinafter, a flat glass particle detecting method in accordance with the present invention will be described as follows. According to the present invention, the flat glass particle detecting method comprises the steps of: a first step of obtaining a first photographing image by irradiating light on the transparent plate-shaped body 1 containing the defects 4 through the first polarizer 11, allowing the light transmitted through the transparent plate-shaped body 1 to be incident on the second polarizer 13 having a polarization direction in the range of 0° to 20° that is different from that of the first polarizer, and by photographing the light passing through the second polarizer; a second step of obtaining a second photographing image by irradiating the light on the transparent plate-shaped body 1 containing the same defects 4 through the third polarizer 15, allowing the light transmitted through the transparent plate-shaped body 1 to be incident on the fourth polarizer 17 having a polarization direction in the range 70° to 90° of that is different from that of the third polarizer 15, and by photographing the light passing through the fourth polarizer; and a third step of deciding whether the defects 4 attached or contained in the transparent plate-shaped body 1 are malignant particles that influence the glass quality or benign particles that do not influence the glass quality, by comparing the first photographing image with the second photographing image. In this case, it is also possible that the first step and the second step are performed regardless of order or carried out at the same time.

CONSTITUTIONAL EXAMPLE 1

Figure 4:
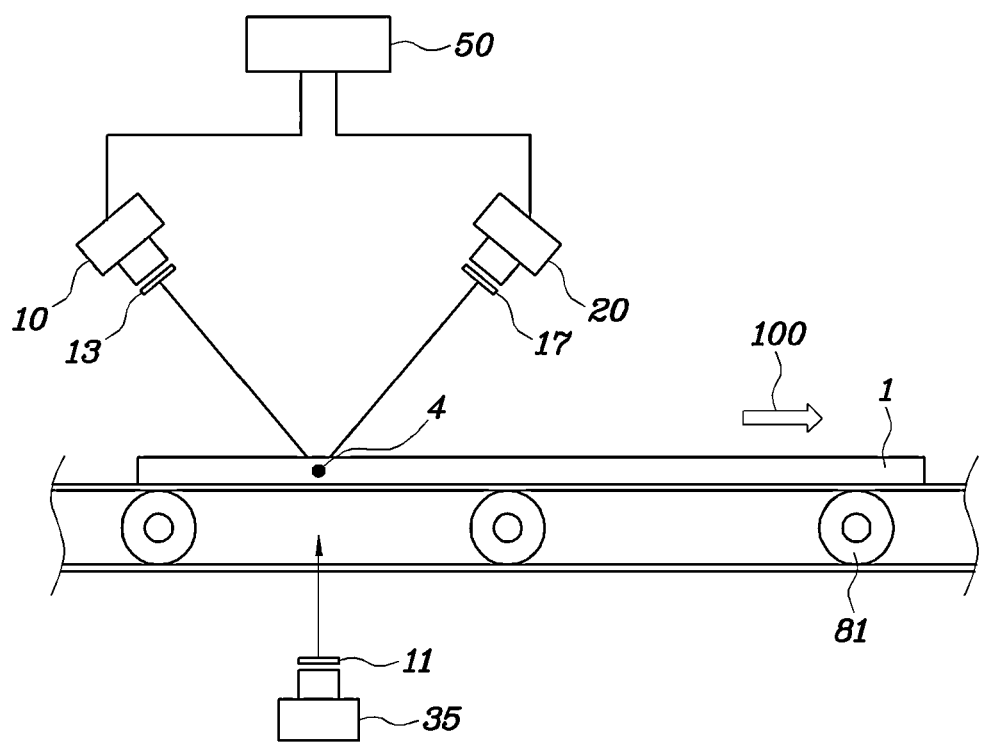
FIG. 4 is a format diagram of an apparatus for detecting particles in flat glass of one embodiment in accordance with the present invention.

FIG. 4 is a format diagram of an apparatus for detecting particles in flat glass of one embodiment in accordance with the present invention. In the embodiment of FIG. 4, one illumination unit 35 is installed in the lower part of a transparent plate-shaped body 1, and a first polarizer 11 having a polarization direction "0°" is equipped between the illumination unit 35 and a lower side of the transparent plate-shaped body 1. Further, a first camera 10 and a second camera 20 are disposed in the upper part of the transparent plate-shaped body 1, and a second polarizer 13 having a polarization direction is "0°" is attached to the front side of the first camera 10, then a fourth polarizer 17 having a polarization direction is "90°" is attached to the front side of the second camera 20. The second polarizer 13 and the fourth polarizer 17 which are attached to the front sides of the first camera 10 and the second camera 20 are adhesively attached to the surface of each lens in film type. An LED lamp capable of irradiating the whole width direction of the transparent plate-shaped body 1 is employed as the illumination unit, and line CCD cameras are used as the cameras 10 and 20. Inline inspection is carried out to inspect the transparent plate-shaped body 1 as transferring the transparent plate-shaped body 1 in the transferring direction 100 by a transferring device 81 such as a conveyor belt or the like. Although FIG. 4 illustrates that the first camera 10 or the second camera 20 is configured as one camera only, it would be understood that a plurality of line camera groups are substantially arranged in a row in the width direction of the transparent plate-shaped body 1.

CONSTITUTIONAL EXAMPLE 2

Figure 5:
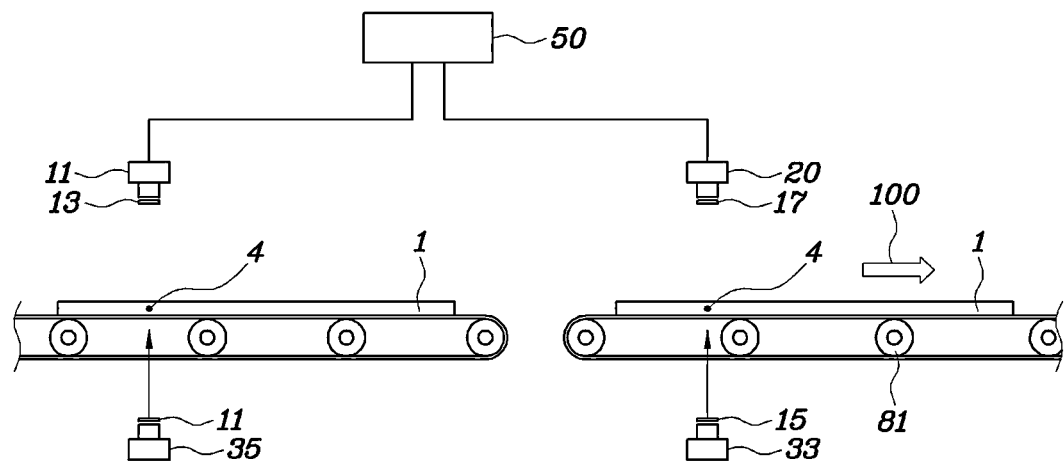
FIG. 5 is a format diagram of an apparatus for detecting particles in flat glass of one embodiment in accordance with the present invention.

FIG. 5 is a format diagram of an apparatus for detecting particles in flat glass of one embodiment in accordance with the present invention. The configuration of FIG. 3 has been applied to the embodiment of FIG. 5. A first photographing device comprises: a first illumination unit 31 installed in the lower part of a transparent plate-shaped body 1; a first polarizer 11 installed between the lower side of the transparent plate-shaped body 1 and the first illumination unit 31, and having a polarization direction "0°"; a first camera 10 positioned in the upper part of the transparent plate-shaped body 1; and a second polarizer 13 positioned on the front side of the first camera 10, and having a polarization direction "0°". The second photographing device comprises: a second illumination unit 33 installed in the lower part of the transparent plate-shaped body 1; a third polarizer 15 installed between the lower side of the transparent plate-shaped body 1 and the second illumination unit 33, and having a polarization direction "0°"; a second camera 20 positioned in the upper part of the transparent plate-shaped body 1; and a fourth polarizer 17 positioned on the front side of the second camera 20, and having a polarization direction "90°".

The second polarizer 13 and the fourth polarizer 17 which are attached to the front sides of the first camera 10 and the second camera 20 are adhesively attached to the surface of each lens in film type. LED lamps capable of irradiating the whole width direction of the transparent plate-shaped body 1 are employed as the illumination units, and line CCD cameras are used as the cameras 10 and 20. Inline inspection is carried out to inspect the transparent plate-shaped body 1 as transferring the transparent plate-shaped body 1 in the transferring direction 100 by a transferring device 81 such as a conveyor belt or the like. In FIG. 5, as the same transparent plate-shaped body 1 is transferred along the transferring direction 100 by using the transferring device 81, a first image is firstly obtained by using the first photographing device, and in the next step, a second image is obtained by using the second photographing device, then a processor 50 distinguishes both images to classify the types of defects.

Although FIG. 5 illustrates that the first camera 10 or the second camera 20 is configured as one camera only, it would be understood that a plurality of line camera groups are substantially arranged in a row in the width direction of the transparent plate-shaped body 1.

EXPERIMENTAL EXAMPLES

FIG. 6 shows photos for photographing flat glass that contains defects with bubble components of 200 um size by using the photographing device configurations suggested in FIG. 4.

FIG. 6(a) shows a photo obtained by a first camera after the flat glass containing the defects with the bubble components of 200 um size is photographed, and FIG. 6(b) shows a photo obtained by a second camera after the flat glass containing the defects with the bubble components of 200 um size is photographed. Like shown in FIG. 6, it would be perceived that when the flat glass having the defects such as the bubble components is photographed, images of the defects with the bubble components are clearly expressed by a photographing device having a parallel polarization direction, but images of the defects 4 with the bubble components are not clearly identified by a photographing device having a vertical polarization direction.

FIG. 7 shows photos for photographing flat glass that contains defects with metal components of 200 um size by using the photographing device configurations suggested in FIG. 4. FIG. 7(a) shows a photo for photographing the flat glass containing the metal defects of 200 um size by a first camera, and FIG. 7(b) shows a photo for photographing the flat glass containing the metal defects of 200 um size by a second photographing device. Like shown in FIG. 7, it would be perceived that when the flat glass having the defects with the metal components is photographed, all the metal defects are identified with the naked eye by a photographing device having a parallel polarization direction and a photographing device having a vertical polarization direction.

Although preferred embodiments of the present invention have been described for illustrative purposes, those skilled in the art will appreciate that various modifications, additions and substitutions are possible, without departing from the scope and the spirit of the invention as disclosed in the accompanying claims.

What is claimed is:

1. An apparatus for detecting particles in a flat glass in the state of transferring to decide whether the particles contained in the flat glass are benign defects including bubbles or malignant defects including metals, comprising:
    a first photographing device, comprising:
        a first illumination unit which is installed in one region selected from upper and lower regions on the basis of flat glass and which illuminates a light obliquely based on the normal vector of the flat glass;
        a first polarizer which is installed between the illumination unit and the flat glass, and has a first polarization direction;
        a first camera which is installed on the normal vector of the flat glass in the opposite direction where the first illumination unit is installed on the basis of the flat glass and which receives the light diffused by defects; and
        a second polarizer which is equipped in a space between the first camera and the flat glass; and
    a second photographing device, comprising:
        a second illumination unit which is installed in same region selected from upper and lower regions on the basis of flat glass and which illuminates a light obliquely based on the normal vector of the flat glass;
        a third polarizer which is installed between the second illumination unit and the flat glass, and has a second polarization direction;
        a second camera which is installed on the normal vector of the flat glass in the opposite direction where the second illumination unit is installed on the basis of the flat glass and which receives the light diffused by defects; and
        a fourth polarizer which is equipped in a space between the second camera and the flat glass;
wherein the first polarizer and the second polarizer have different polarization directions in the range of 0° to 20°, and the third polarizer and the fourth polarizer have different polarization directions in the range of 70° to 90°, wherein the light illuminated from the first illumination unit and the second illumination unit does not enter directly to the first camera and the second camera respectively, and the light being obliquely illuminated from the first illumination unit and the second illumination unit directly to the first polarizer and the third polarizer, respectively, and directly from the first polarizer and the third polarizer to the flat glass.

2. The apparatus of claim 1, wherein
the second polarizer and the fourth polarizer are attached to the front lenses of the first camera and the second camera in film type.

3. The apparatus of claim 1, wherein
a transferring device for transferring the flat glass is further comprised.

4. The apparatus of claim 1, wherein
the first camera and the second camera are configured as a plurality of line CCD cameras, respectively.

5. The apparatus of claim 1, wherein
the second polarizer has the same polarization direction as that of the first polarizer.

6. The apparatus of claim 1, wherein
the fourth polarizer has a polarization direction vertical to that of the first polarizer.

7. The apparatus of claim 1, wherein
the flat glass is for protecting a solar cell.

8. A flat glass particle detecting method for distinguishing whether defects contained in flat glass are benign particles including bubbles or malignant particles including metals, comprising the steps of:

a first step of obtaining an image by irradiating polarized light obliquely based on the normal vector of the flat glass on the flat glass, and by photographing light transmitted directly from an illumination unit and to and through a polarizer which has a polarization direction in the range of 0° to 20° that is different from a polarization direction of the polarized light;

a second step of obtaining an image by irradiating polarized light obliquely based on the normal vector of the flat glass on the flat glass, and by photographing light transmitted directly from an illumination unit and to and through a polarizer which has a polarization direction in the range of 70° to 90° that is different from the polarization direction of the polarized light; and a third step of distinguishing whether defects contained in the flat glass are malignant particles that affect the glass quality or benign particles that do not affect the glass quality, by comparing the image obtained from the first step with the image obtained from the second step, wherein the first step and the second step are carried out at the same time or performed regardless of order.

9. The method of claim 8, wherein
the polarization direction of the polarized light is matched with the polarization direction of the polarizer in the first step.

10. The method of claim 8, wherein
the polarization direction of the polarized light is vertical to the polarization direction of the polarizer in the second step.

11. The method of claim 8, wherein
the flat glass is for protecting a solar cell.

* * * * *